United States Patent [19] [11] 4,131,081
Terashima [45] Dec. 26, 1978

[54] TONER CONCENTRATION DETECTING APPARATUS

[75] Inventor: Isamu Terashima, Hitachi, Japan
[73] Assignee: Hitachi, Ltd., Japan
[21] Appl. No.: 783,554
[22] Filed: Apr. 1, 1977
[30] Foreign Application Priority Data
Apr. 14, 1976 [JP] Japan .................................. 51-41352
[51] Int. Cl.² ........................................... G03G 15/09
[52] U.S. Cl. ......................................... 118/646; 118/9
[58] Field of Search ....................... 118/9, 646, 658, 7; 222/DIG. 1

[56] References Cited
U.S. PATENT DOCUMENTS

| | | | |
|---|---|---|---|
| 3,527,651 | 9/1970 | Shelffo et al. | 118/646 X |
| 3,572,551 | 3/1971 | Gillespie | 118/646 X |
| 3,698,926 | 10/1972 | Furvichi | 118/646 X |
| 3,802,381 | 4/1974 | O'Neill et al. | 118/646 X |
| 3,835,380 | 9/1974 | Webb | 118/9 X |
| 3,892,672 | 7/1975 | Gawron | 118/646 X |
| 3,911,864 | 10/1975 | Hudson | 118/658 X |
| 3,999,687 | 12/1976 | Baer et al. | 222/DIG. 1 X |

Primary Examiner—Werner H. Schroeder
Assistant Examiner—Andrew M. Falik
Attorney, Agent, or Firm—Craig & Antonelli

[57] ABSTRACT

A toner concentration detecting apparatus is disclosed wherein developing powder including magnetic carrier and pigmented toner is carried on a magnet roller and transported thereby to a surface of a photosensitive drum, and after development a portion of the developing powder is removed off the surface of the magnet roller and passed through a detection coil to determine a concentration of the toner in the developing powder based on a magnitude of an inductance of the detection coil. Accuracy of detection is enhanced by magnetizing the developing powder into chain at areas upstream and downstream of the detection coil and demagnetizing the developing powder within the detection coil. By magnetizing the developing powder into chain upstream and downstream of the detection coil, the stream of developing powder within the detection coil is stabilized and the variation of the developing powder density within the detection coil is minimized.

13 Claims, 3 Drawing Figures

TONER CONCENTRATION DETECTING APPARATUS

BACKGROUND OF THE INVENTION

1. Field of the Invention

The present invention relates to an apparatus for detecting a toner concentration (composition ratio) in developing powder in an electrostatic printing machine which uses the developing powder comprising a mixture of magnetic carrier and toner.

2. Description of the Prior Art

In an apparatus in which an electrostatic latent image is developed by developing powder comprising the mixture of the magnetic carrier and the toner, only the toner is consumed in the developing process but the magnetic carrier is not substantially consumed but it is maintained for reuse. As a result, as the developing powder is used repeatedly, a toner concentration of the developing powder decreases gradually. In order to maintain a high quality of the developed image, however, the toner concentration should be maintained at a fixed value or in a given range. Accordingly, it is necessary to detect the toner concentration. It has been proposed to utilize a change in permeability of the developing powder in order to detect the toner density, an example of which is U.S. Pat. No. 3,572,551 "Apparatus for Monitoring and Controlling the Concentration of Toner in a Developer Mix" to Henderson et al, application Ser. No. 811,132 filed Mar. 27, 1969, issued Mar. 30, 1971 and assigned to RCA.

In the conventional apparatus, however, a separate drive means for forcibly recirculating the developing powder has been required in addition to the developing apparatus, and the accuracy of detection was low when the toner concentration was measured in such a forcibly recirculated system.

SUMMARY OF THE INVENTION

It is object of the present invention to provide a toner concentration detecting apparatus capable of detecting the toner concentration with a high accuracy.

It is other object of the present invention to provide a toner concentration detecting apparatus which can be readily mounted in an existing developing apparatus.

Briefly, according to the present invention, in transporting the developing powder to a magnetically responsive device, the developing powder is magnetized into chain at downstream of the magnetically responsive device to facilitate the transport, and the magnetization of the developing powder is released in an active region of the magnetically responsive device for preventing external magnetic flux from acting on the magnetically responsive device.

DETAILED DESCRIPTION OF THE PREFERRED EMBODIMENTS

Figure 1:
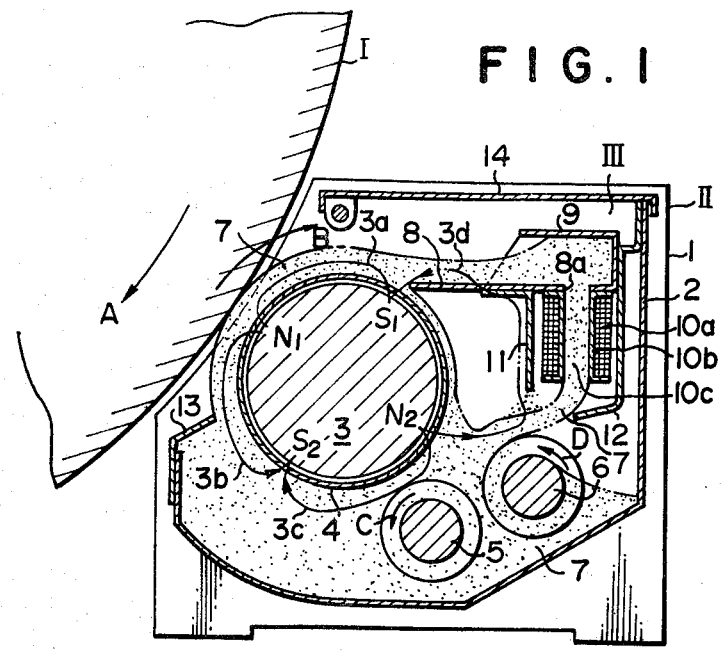
FIG. 1 is a longitudinal sectional view of major sections of a developing apparatus incorporating detecting apparatus of the present invention.
Figure 2:
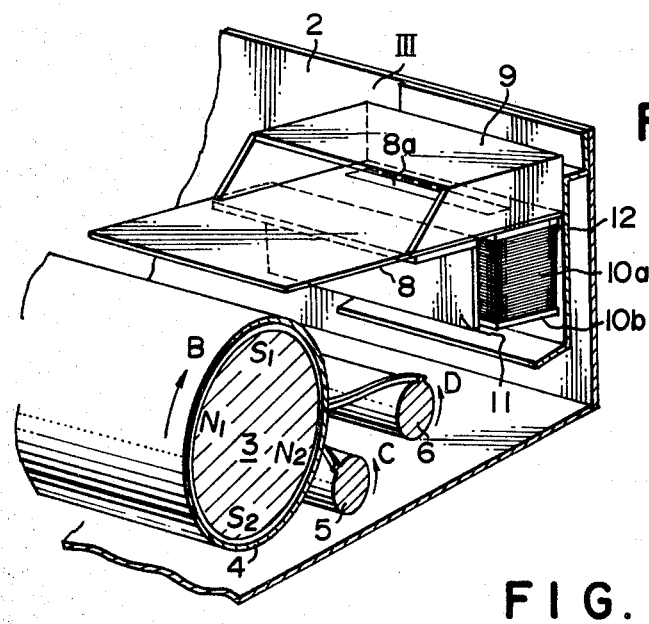
FIG. 2 shows a perspective and longitudinal sectional view of major sections of said developing apparatus with developing powder being removed.

Referring to FIGS. 1 and 2, numeral I denotes a photosensitive drum, on a surface of which a electrostatic latent image is formed by a well-known electronic photography technology. Numeral II denotes a developing apparatus which uses developing powder and which incorporates a toner concentration detecting apparatus III of the present invention.

The developing apparatus II has a pair of side plates 1 and a case 2 which define a chamber to receive developing powder 7 at the bottom portion thereof. The developing powder 7 includes powdered magnetic carrier and toner. Numeral 3 denotes a permanent magnet roll or bar supported between the pair of side plates 1 and is circumferentially magnetized. Numeral 4 denotes a sleeve of non-magnetic material arranged concentrically to the permanent magnet 3 and rotatably supported. Numerals 5 and 6 denote blending screws for blending or agitating the developing powder 7 and rotatably supported between the pair of side plates 1. The photosensitive drum I, sleeve 4 and the blending screws 5 and 6 are linked by an external driving mechanism, not shown, such that they are synchronously driven.

In the toner concentration detecting apparatus III, numeral 8 denotes a developing powder guide plate made of non-magnetic material, and end of which is arranged to face the outer periphery of the sleeve 4 with a slight clearance therebetween to divert a portion of the developing powder transported along the outer periphry of the sleeve 4. Numeral 9 denotes a cover formed at the rear of the developing powder guide plate 8 to maintain the amount of the developing powder transported over the guide plate 8 to a fixed amount. Numeral 10a denotes a detection coil wound on a hollow bobbin 10b which is mounted on the underside of the guide plate 8 such that an aperture 8a formed at a rear end of the guide plate 8 aligns to an aperture 10c of the bobbin 10b. The bobbin 10b is made of non-magnetic material and a projection of the center aperture 10c is of rectangular shape. Numeral 11 denotes a magnetic by-pass plate of magnetic material having an L-shape, one leg of which is mounted on the underside of the guide plate 8 near the entry of the cover 9 and the other leg of which depends parallely with the bobbin 10b and extends near the top of the magnetic powder 7 at the bottom of the chamber. Numeral 12 denotes a baffle board for directing the flow of the developing powder from the bobbin 10b into the sleeve 4 and the blending screw 6 and it is made of non-magnetic material. Those elements are integrally coupled and the entire assembly is mounted in the case 2 by the baffle board 12.

Numeral 13 denotes a restricting plate for restricting the thickness of the developing powder layer transported by the sleeve 4 by being deposited thereon by magnetic attraction force of the magnet 3, to a fixed thickness such that the outer surface of the developing powder layer slightly rubs the surface of the photosensitive drum I. Numeral 14 denotes a cover for preventing the scatter of the developing powder 7 and it is pivotably mounted.

As the photosensitive drum I rotates in the direction of an arrow A, the sleeve 4 and the blending screws 5 and 6 rotate in the directions of arrows B, C and D, respectively. On the other hand, lines of magnetic force of the permanent magnet 3 are produced between magnet poles $S_1$, $S_2$, $N_1$, $N_2$ as shown by arrows 3a to 3d. As a result, the magnetic powder 7 is strongly attracted onto the sleeve 4 at the areas between magnet poles $S_1$-$N_1$-$S_2$-$N_2$, forming magnetic brushes. As the sleeve 4 rotates in the direction of the arrow B, the developing powder layer also moves in the same direction so that the outer periphery of the layer contacts the photosensitive drum I to develop a latent image thereof. Thereafter, when the developing powder layer reaches immediately above the magnet pole $S_1$, it is partially deverted from the surface of the sleeve 4 by the guide plate 8 and the diverted developing powder is transported on the guide plate 8 toward the cover 9. Since the bypass plate 11 is arranged between the entry of the cover 9 and the developing powder 7 at the bottom of the chamber, the line of magnetic force 3d between the magnet poles $S_1$ and $N_2$ primarily passes from the magnet pole $N_2$ through the developing powder 7 at the bottom of the chamber, the bypass plate 11, the developing powder 7 on the guide plate 8 to the magnet pole $S_1$, and does not pass through the aperture 10c of the bobbin 10b. Thus, the developing powder 7 in the area from the surface of the sleeve to the vicinity of the entrance of the cover 9 is magnetized into chain so that the developing powder on the guide plate is pushed by that on the sleeve to facilitate smooth transport of the developing powder to the cover. 9. The magnetic powder 7 which has entered in the cover 9 is released from magnetic binding and the attraction forces among the magnetic carriers are substantially nullified. As a result, the developing powder 7 flows down through the center aperture 10c of the bobbin 10b in a free state. The developing powder 7 passed through the aperture 10c is baffled by the baffle plate 12 located near the aperture 10c and again magnetized into chain by the magnetic flux passing through the bypass plate 11 and passed toward the magnet pole $N_2$. Thus, by magnetizing the developing powder 7 into chain upstream and downstream of the bobbin 10b to transport in the chained state, the stream of the developing powder 7 within the bobbin 10b is stabilized and the variation of the developing powder density within the bobbin is minimized. Furthermore, the action of the external magnetic flux to the coil 10a is prevented. When the rotation of the photosensitive drum I is stopped, the movement of the developing powder is also stopped so that the inside of the bobbin is not emptied.

Figure 3:
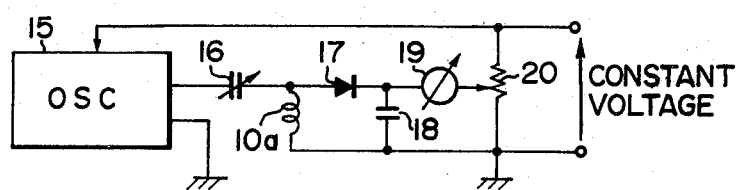
FIG. 3 shows an electric circuit including the detection coil for indicating a detected concentration.

The coil 10a wound on the bobbin 10b exhibits an inductance determined by a permeability of the developing powder 7 flowing through the aperture 10c. Thus, as shown in FIG. 3, a series circuit of the coil 10a and a capacitor 16 is connected across output terminals of a constant frequency oscillator 15 (of the order of 100 KHz), and a voltage across the coil 10a is rectified by a diode 17 and filtered by a capacitor 18. A difference between a voltage across the capacitor 18 and a reference voltage across a potentiometer 20 is indicated by a meter 19 to indicate a detected concentration of the developing powder 7 relative to a reference concentration. The constants of the capacitor 16 and the coil 10a are selected such that a resonance frequency thereof is slightly staggered from the output frequency of the oscillator 15 when the toner concentration is at the reference value, so that a large change in the inductance of the coil (i.e. voltage across the coil) is produced by the reduction of the toner concentration of the developing powder. By setting the voltage across the capacitor 18 produced at the reference toner concentration to be equal to the output voltage across the potentiometer 20, and using a center zero type meter as the meter 19, the excess or shortage of the detected toner concentration relative to the reference toner concentration can be indicated.

In the embodiment illustrated, the detection coil may be replaced by a magnetically responsive semiconductor device. In this case, magnetic flux is caused to pass from a reference magnet to the developing powder flowing through the aperture 10c of the bobbin 10a and a change of magnetic flux due to reluctance change is utilized. The guide plate 8 need not divert the developing powder 7 over the entire axial width of the sleeve 4 but it may sample the developing powder 7 from a portion of the area of the developing powder actually used for the development of latent image. However, a larger axial dimension of the layer of the developing powder 7 passing through the detection coil 10a is advantageous in preventing the offset of the detection. As a modification, the indication meter 19 may be replaced by a solenoid valve to automatically supply toner to the developing powder.

I claim:

1. An apparatus for detecting a toner concentration of developing powder comprising a mixture of magnetic carrier and toner comprising:
    a transport means for transporting the developing powder stored in a chamber while magnetically attracting the developing powder;
    a hollow body;
    a guide means for diverting a portion of said developing powder from said transport means and directing the diverted developing powder to said hollow body;
    means for producing a magnetic path sufficiently closely positioned to the downstream side of said hollow body for magnetizing the developing powder downstream of said hollow body to stabilize the flow of the developing powder passing through said hollow body; and
    a response means for responding to a permeability of the developing powder passing through said hollow body.

2. An apparatus for detecting a toner concentration according to claim 1 wherein said response means comprises a coil wound on said hollow body.

3. An apparatus for detecting a toner concentration according to claim 1 wherein said means for producing said magnetic path includes a magnetic bypass plate extending from an underside of said guide means to a bottom of said hollow body along said hollow body.

4. An apparatus for detecting a toner concentration according to claim 1 wherein a baffle plate is provided to deflect the developing powder that has passed through said hollow body in the direction of said magnetic path.

5. An apparatus for detecting a toner concentration of developing powder comprising a mixture of magnetic carrier and toner comprising:
    a transport means for transporting the developing powder stored in a chamber while magnetically attracting the developing powder;
    a hollow body;
    a guide means for diverting a portion of said developing powder from said transport means and directing the diverted developing powder to said hollow body;

means for producing a magnetic path sufficiently closely positioned to the upstream and downstream sides of said hollow body for magnetizing the developing powder upstream and downstream of said hollow body to stabilize the flow of the developing powder passing through said hollow body; and a response means for responding to a permeability of the developing powder passing through said hollow body.

6. An apparatus for detecting a toner concentration according to claim 5 wherein a baffle plate is provided to deflect the developing powder that has passed through said hollow body in the direction of said magnetic path.

7. In an electronic photograph machine wherein developing powder comprising magnetic carrier and toner is magnetically attracted on a surface of a non-magnetic sleeve which rotates around a permanent magnet, to transport the developing powder to develop a latent image, a toner concentration detecting apparatus comprising:

a non-magnetic hollow body;
a coil wound on said hollow body;
a guide plate for diverting a portion of said developing powder on an outer periphery of the sleeve at an area downstream of a developing station and directing the diverted developing powder toward said hollow body;
a magnetic bypass plate arranged in parallel with said hollow body for bypassing magnetic flux flowing in said developing powder at regions upstream and downstream of said hollow body; and
a electric circuit responsive to an inductance of said coil.

8. A toner concentration detecting apparatus according to claim 7 wherein said hollow body has a center aperture of an elongated rectangular section extending axially of said sleeve.

9. A toner concentration detecting apparatus according to claim 7 wherein said guide plate is made of non-magnetic material having an end arranged in proximity to said sleeve and a rear end at which an aperture communicating with said hollow body is formed.

10. A toner concnetration detecting apparatus according to claim 7 wherein said magnetic bypass plate extends from an intermediate section of said guide plate to an exit of said hollow body along said hollow body.

11. A toner concentration detecting apparatus according to claim 7 wherein one end of said guide plate is arranged above a magnet pole of one polariry of said magnet in said sleeve, and a baffle board is arranged at an exit of said hollow body for directing the flowing developing powder toward a magnet pole of other polarity of said magnet.

12. In an apparatus for detecting a toner concentration of developing powder comprising a mixture of magnetic carrier and toner wherein the developing powder is passed through a hollow body and wherein means are provided for responding to a permeability of the developing powder passing said hollow body, the improvement comprising means for providing a magnetic path sufficiently closely positioned to the downstream side of said hollow body for magnetizing the developing powder to stabilize the flow of the developing powder passing through said hollow body.

13. The apparatus of claim 12 wherein said means for providing said magnetic path magnetizes the developing powder upstream and downstream of said hollow body to stabilize the flow of the developing powder passing through said hollow body.

* * * * *